United States Patent [19]

Pollner et al.

[11] 4,021,326
[45] May 3, 1977

[54] ELECTRO-CHEMICAL SENSOR

[75] Inventors: Rudolf Pollner, Kornwestheim; Karl-Hermann Friese, Leonberg; Bernhard Topp, Gerlingen; Horst Neidhard, Korntal, all of Germany

[73] Assignee: Robert Bosch G.m.b.H., Gerlingen-Schillerhohe, Germany

[22] Filed: Mar. 4, 1974

[21] Appl. No.: 447,475

Related U.S. Application Data

[63] Continuation-in-part of Ser. No. 259,134, June 2, 1972, abandoned.

[30] Foreign Application Priority Data

Mar. 7, 1973 Germany ............................ 2311165

[52] U.S. Cl. .......................................... 204/195 S
[51] Int. Cl.$^2$ ................................... G01N 27/46
[58] Field of Search .......... 204/195 S, 1 T; 324/29; 60/276; 123/119 R

[56] References Cited

UNITED STATES PATENTS

| | | | |
|---|---|---|---|
| 3,347,767 | 10/1967 | Hickam | 204/195 S |
| 3,403,090 | 9/1968 | Tajiri et al. | 204/195 S |
| 3,468,780 | 9/1969 | Fischer | 204/195 S |
| 3,503,809 | 3/1970 | Spacil | 204/195 S |
| 3,578,578 | 5/1971 | von Krusenstierna | 204/195 S |
| 3,645,875 | 2/1972 | Record et al. | 204/195 S |
| 3,654,112 | 4/1972 | Beekmans et al. | 204/195 S |
| 3,841,987 | 10/1974 | Friese et al. | 204/195 S |

OTHER PUBLICATIONS

J. D. Tretjakow et al., Berichte der Bunsengeselchaft, vol. 69, No. 5, pp. 396–402, (1965).

*Primary Examiner*—G. L. Kaplan
*Attorney, Agent, or Firm*—Flynn & Frishauf

[57] ABSTRACT

Electro-chemical sensor to determine oxygen concentration in hot internal combustion exhaust gases in the form of a closed, tubular element having a solid ion conductive electrolyte; an electron-conductive coating on the inner surface thereof; a porous or fissured electron conductive layer on the outer surface of said solid electrolyte or on a part of said surface, part of the pores or fissures being macroporous, said layer being of a material which catalyzes the formation from said hot exhaust gases of those compounds that are thermodynamically stable at the exhaust temperature; and a porous protective electrically insulating coating on said porous electron-conductive layer. Preferably, a top coating of a heat-resistant metal is applied, which top coating has additionally properties to act as a getter with respect to poisons affecting the catalyzing material.

26 Claims, 3 Drawing Figures

U.S. Patent  May 3, 1977  4,021,326
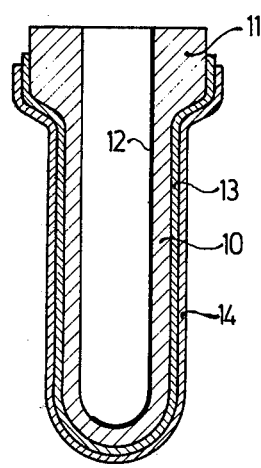
Fig. 1
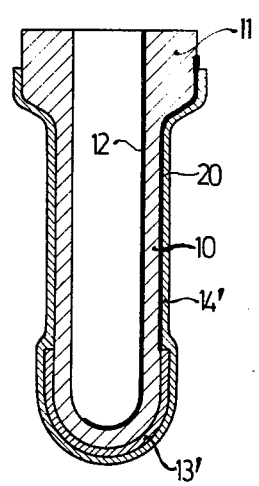
Fig. 2
Fig. 3
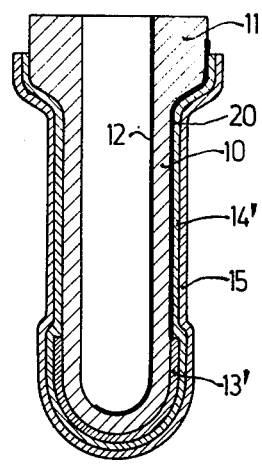

ELECTRO-CHEMICAL SENSOR

Reference is made to the following related applications which are hereby incorporated herein: U.S. Pat. No. 300,047, filed Oct. 24, 1972, now U.S. Pat. No. 3,827,327 issued Aug. 6, 1974, assigned to the Assignee of the present application; and U.S. Ser. No. 259,134, filed June 2, 1972, now abandoned in favor of Continuation Application Ser. No. 508,250, filed Sept. 23, 1974, also assigned to the Assignee of the present application. The present application is a Continuation-in-part of said earlier application Ser. No. 259,134.

The present invention relates to an electro-chemical sensing element to determine oxygen content in fluids, and more particularly to determine the oxygen content in the exhaust gases of internal combustion engines.

Electro-chemical sensors which are oxygen concentration cells with a solid electrolyte which is ion conductive, and having an electron conductive layer applied to the outer surfaces, have previously been proposed. Internal combustion engines, and particularly automotive-type internal combustion engines, in operation, produce exhaust gases in which carbon monoxide, nitrogen-oxygen compounds, and non-combusted, or incompletely combusted hydrocarbon compounds are present. All these exhaust gases contribute to air pollution. To reduce the polluting components from internal combustion engines, and thus to decrease general air pollution, it is necessary to remove noxious components from the exhaust gases of internal combustion engines to the greatest extent possible. Primarily, carbon-oxygen and carbon-hydrogen compounds should be brought to the highest possible oxidation stage, that is, $CO_2$ and water. $NO_x$ components should be converted to elementary nitrogen.

The noxious components in the exhaust gases of automotive engines may, for example, be converted to harmless compounds such as $CO_2$, nitrogen, and water, by subjecting the exhaust gases to after-burning and conducting the exhaust gases at temperatures above about 300° C over a catalyst. In order to successfully carry out the conversion, it is necessary, however, that the composition of the exhaust gases is so adjusted that it is possible to substantially completely convert the exhaust gases to the harmless compounds. The ratio of air to fuel must, therefore, be approximately stoichiometric. This relationship has, in the past, been characterized by a value of $\lambda = 1$, that is an air number of unity. With respect to the oxygen content of the exhaust gases, an air number of $\lambda \leq 1$ means that there is no excess oxygen present which exceeds the balanced mass relationship of the various possible reactions. If the air number exceeds 1.0, that is, $\lambda > 1$, there will be excess oxygen in the mixture. The exhaust gas changes from reducing to oxidizing state at $\lambda = 1.0$.

To maintain a value of $\lambda = 1$, it is necessary to provide a sensing element in the path of the exhaust gases, that is, exposed to the exhaust gases, the sensing element being so constructed that it can determine the oxygen content of the exhaust gases. The output signal from the sensing element is then applied to a controller which so controls the air-fuel mixing device (carburetor or fuel injection system) for the internal combustion engine that the exhaust gases will have the proper composition, that is, have minimum noxious components.

Measuring or sensing elements utilize the principle of oxygen concentration cells with an ion conductive solid electrolyte. The prior art discloses electrodes comprising a solid electrolyte covered, at least in part, on both sides with platinum. This sensor when used to measure oxygen concentration in exhaust gases delivers output signals depending on relative oxygen concentration in the exhaust gases with respect to ambient air. It has been found, however, that the voltage jump at $\lambda = 1$ is not sharp and pronounced; rather, the voltage changes over a substantial range of air number values, providing a gradual variation in output potential depending on oxygen content in the exhaust gases, with respect to ambient air. These sensors, when combined with control systems should, however, provide a sharp voltage change at $\lambda = 1$; it is of substantial advantage if this voltage jump is pronounced and precise at an air number of unity.

It is an object of the present invention to provide improved electro-chemical sensing devices to determine oxygen concentration, particularly in the exhaust gases of internal combustion engines, which provide a sharp voltage jump at a value of $\lambda = 1$, that is, when the air number is unity, which have short response time, and are reliable and durable under the rough and varied operating conditions encountered in automative use.

Subject matter of the present invention: The electron conductive layer which catalyzes the formation of the thermodynamically stable gases from the hot exhaust, is formed with pores or fissures which have a diameter, or width which extends to an order of magnitude comparable to that of the thickness of the layer. The electron conductive layer and any outer surface of the solid electrolyte which is not covered by the electron conductive layer is coated with one or more porous coatings or a conbination of cover coatings. This porous coating can be on the electron conductive layer and on any portion of the solid electrolyte surface not covered by the electron conductive layer.

Oxygen concentration cells, in principle, can determine the remaining, or excess oxygen content in the exhaust gases, as well as the oxygen content of the components of the exhaust gases which are thermodynamically stable, i.e., in thermodynamic equilibrium at the service temperature.

Sharp potential jumps can usually be obtained only when the components of the exhaust gases are thermodynamically stable. Under ordinary conditions, this is hardly ever the case.

The (uncombined) or excess oxygen in the exhaust system, that is, the oxygen contained in the exhaust gases due to incomplete oxidation, is measured by an oxygen concentration cell having the solid slectrolyte contacted with catalytically inactive metals, or inactive electron conductive oxides. Such cells measure a roughly uniform change in voltage as the exhaust gases change from lean ($\lambda < 1$) to richer ($\lambda < 1$) mixture. This transition is not unambiguously defined, since the content of excess oxygen in the exhaust gases is not a fixed unambiguously predetermined function of temperature, and of the air-fuel ratio. The excess oxygen content in the exhaust gases, which is measured by such oxygen cells, depends, among other parameters, on the characteristics of the engine, temperature, speed of gas flow past the solid electrolyte surface and on various other parameters.

The relationship of signal, that is, of voltage, with respect to air number λ becomes reproducible when the oxygen content of those oxygen-containing components of the exhaust gases which are thermodynamically stable at the service temperature, is measured. The voltage E from the sensing element is determined, in accordance with the Nernst relationship, solely by temperature, and the equilibrium oxygen content in the exhaust gases. At λ = 1 that is, upon transition between reducing and oxidizing atmosphere, a clearly noticeable voltage jump of several 100 mV is characteristic. The position of this voltage jump at λ = 1 is independent of temperature. The amplitude of the voltage jump, however, depends on temperature and may be in the range of from about 300 mV to 400 mV.

In said U.S. Ser. No. 259,134, it has been proposed to measure the oxygen content of thermodynamically stable compounds, by means of a sensor in which a solid electrolyte surface is provided with a surface layer which catalyzes the formation of the gas equilibrium, i.e., the thermodynamically stable oxygen-containing compounds at the service temperature of the exhaust gases, i.e., 450° C and higher. Larger pores, that is macropores, and other surfaces directly exposed to the exhaust gases were deemed undesirable, since excess oxygen molecules could then directly contact the solid electrolyte surface, and thus mixed, or composite voltages were measured. The concept of micropores was, thus, so limited that micropores or microfissures were defined to have a diameter, or width which is less than half the average thickness of this catalyzing layer.

In accordance with the present invention it has been found that the layer which catalyzes the gas equilibrium may have larger pores or fissures in addition to the micropores mentioned above if it is coated by a single or multiple layer cover coating. Permitting the pores to have greater dimensions substantially facilitates the manufacture of these layers, since it is difficult to avoid making the layers with pores which were greater than those which were defined as micropores, so that, as a result, the change of voltage at λ = 1 was flattened, providing a less pronounced sharpness of transition at the air number of unity. Sensors, in which larger pores occurred in the catalytically active layer, thus, can be made which need no longer be rejected for use; rather, they can be used as sensors similar to those that have no large pores at all if, in accordance with the present invention, they are covered with a porous cover coating.

The invention will be described by way of example with reference to the accompanying drawings, wherein the three Figures illustrate longitudinal sectional views through sensors in accordance with the present invention, and showing different embodiments and arrangements of the respective layers and coatings.

FIG. 1: The outer surface is completely covered by a platinum layer. A solid electrolyte body, essentially comprising zirconium dioxide with a wall thickness of 0.5 to 1 mm is formed into a closed tube 10. The open end of the body 10 is circumferentially enlarged to form a boss, or flange 11. An inner electrode 12 is located at the inside of the tube. This electrode 12 may, for example, be a conductive track, coating, or strip made of a noble metal, or of a material which is electron conductive when operating temperature has been reached, for example, a simple, or a compound oxide. In the illustrated embodiments it is a conductive layer of platinum. The outer surface of the solid electrolyte tube 10 is completely covered by a layer of platinum 13. The platinum layer 13 extends to the flange 11. The thickness of the platinum layer 13 is approximately 5 μm. It has macropores up to about 3 μm diameter. The platinum layer is coated with a porous electrically insulating coating of magnesium spinel 14. The thickness of the magnesium spinel coating is about 50 μ m. The magnesium spinel coating 14 terminates just short of the termination of the platinum layer 13, on the flange 11, to permit attachment of an electrical connection to layer 13.

A sensor made in accordance with FIG. 1 but prior to application of the magnesium spinel coating has a transition characteristic, that is, exhibits a voltage between extreme output values which is rather flat, that is, is not sharply defined at λ = 1. Coating the sensor with the magnesium spinel coating 14, however, provides a sensor which exhibits a voltage jump comparable to one in which the pores in the platinum layer 13 were measured to be smaller than 0.1 μm; thus, the characteristic steep voltage jump at the transition point of λ = unity of a micropore sensor was obtained, although the pores in the platinum layer 13 were partially macropores.

FIG. 2: The solid electrolyte body 10, inner electrode 12 are similar to the sensor of FIG. 1. Platinum layer 13' is applied only to the lower portion of body 10, however. A conductor strip 20, of thin electrically conductive foil, conductive paint, or the like, and electrically connected to layer 13', extends at the circumference of body 10 to the flange 11 to provide an electrical connection. Strip 20 may, for example, be made by applying a platinum suspension, in strip form, to the outside of body 10, and extending to flange 11. The entire remaining portion of the outer circumference, as well as the platinum layer 13', and including the connecting strip 20, are covered by the porous coating 14', comprising magnesium spinel. The magnesium spinel terminates just short of the terminal end of the strip 20 to permit electrical connection thereto adjacent the end of the sensor. The operating results obtained are similar to those obtained with the sensor of FIG. 1; substantially less platinum is, however, required in the construction of the sensor of FIG. 2.

FIG. 3 illustrates a sensor similar to FIG. 2 in which a cover coating 15 is applied on top of the porous coating 14'. This cover coating is a chrome (chromium metal) layer, which is porous. Its thickness is about 50 μm (micro-meter). The cover coating may be applied by plasma spray (jet) methods.

The production steps, to make certain parts of the electrodes of FIGS. 1 to 3, e.g., solid electrolyte, the various platinum layer, and the porous protective cover are disclosed in said U.S. Ser. No. 259,134.

It is believed that the advantageous effect of the porous coating 14—the use of which permits utilization of sensors which previously had been deemed rejects—is due to the gas molecules in the exhaust gases becoming well mixed in the suitably thick porous layer before reaching by diffusion the three-phase boundary of gas—solid electrolyte—electrode. They thereby become homogeneous which increases the reaction speed. Further, the residence time of the exhaust gas molecules capable of reaction on the catalytically active electrode material is increased because the molecules are forced to diffuse along the catalytically active layer due to the porosity of the cover coating 14. They are therefore already converted before they reach the macropores. The macropores are additionally covered by particles (part) of the porous cover coating 14 and provide access to the three-phase boundary only over small gaps. The electron conductive layer 13, in the Figures, which may be built up of one or more individual layers may be platinum, palladium, or iridium, or alloys thereof, and/or an alloy of one of the foregoing with aluminum, cobalt, chromium, or other platinum metals. Alternately, they may be oxide systems, such as copper-chromium oxide, possibly doped with barium oxide; or nickel oxide; or of lanthanum-cobalt-oxide, possibly doped with strontium-oxide. The macropores, i.e. those pores the diameter of which is greater than one half the thickness of the layer, may have an area up to 50% of the geometrical area being coated with the electron conductive layer 13. The thickness of the catalyzing layer is between 0.1 and 50 $\mu$ m and preferably between 0.2 and 20 $\mu$ m.

The porous cover coating 14 comprises an electrically insulating material. Oxides or mixed oxides such as magnesium spinel are preferred (FIG. 1). Mixtures of several oxides, silicate-containing materials such as high-melting sinter glass, refractory ceramic materials like kaolin, and talcum may be used, preferably with the addition of fluxes, such as feldspar, nephelite-syenite or wollastonite. The refractory ceramic materials may be applied in the form of the raw material mixtures, and subsequently sintered. The thickness of the porous layer 14 may be between 0.1 and 500 $\mu$ m; the ratio of thickness of the layer to diameter of pores ist between 2 : 1 and 100 : 1, preferably 5 : 1 and 20 : 1, the pore area may be between 10 and 50%.

It has previously been proposed in said U.S. Ser. No. 259,134 to completely coat the solid electrolyte surface with the catalytically active, electronconductive layer. It has also been proposed in said U.S. Ser. No. 259,134 to coat only a portion of the solid electrolyte exposed to the exhaust gases with such a coating, and the remaining portion of the solid electrolyte surface then being covered by a gas-tight, electrically insulating ceramic protective cover, such a glaze.

If the solid electrolyte body, exposed to the exhaust gases, is only partially covered with a catalytically active electron conductive layer 13, that is if the embodiments of FIGS. 2 and 3 are selected, the remaining surface of the solid electrolyte which may partially or entirely be surrounded by said electron conductive layer 13, i.e. if there are holes in the layer 13, is preferably coated with the same porous coating 14 as previously described as the coating 14' for the catalytically active layer 13. The remaining surface may also be coated with a layer of another electrically insulating material, this layer being gastight or having the same or a smaller porosity than the layer coating the catalytically active layer 13. The extension of this coating 14' (FIGS. 2, 3) to surround the solid electrolyte body 10 prevents formation of a coating or layer on the free solid electrolyte surface by particles and dirt contained in the exhaust gases, which form an electron conductive, catalytically active coating or layer, resulting in stray voltages which lead to a flattening of the response curve and "smear" of the transition of voltage at $\lambda = 1$, and thus detract from the desired sharp transition voltage at $\lambda = 1$. Solid particles which may precipitate need not be contained, as such, in the exhaust gases. They may form gaseous organic or metal organic compounds on the solid electrolyte surface, condensing on the solid electrolyte surface which is colder than the exhaust gas.

Reactions of gaseous compounds with zirconium dioxide, or with fluxes in the ceramics may occur; the reaction products are usually electron conductive and, if precipitated on the solid electrolyte surface, lead to a flattening of the transition characteristics at $\lambda = 1.0$.

The porous coating 14 (or 14') is applied both to the solid electrolyte body 10, as well as to the electron conductive layer 13 (FIG. 1), and conductive strip 20 (FIGS. 2, 3) by sintering, flame spraying plasma spraying, by means of thin-layer techniques, such as thermal vaporizing, precipitation from gases, or by reactive vapor deposition. It layers between 0.1 and 10 $\mu$ m are to be applied, thin-layer technology is preferred; in thicknesses between about 15 and 500 $\mu$ m, application by means of sintering, or flame spraying or plasma spraying is preferred.

The porous electrically insulating coating 14 (or 14') is preferably covered by a further protective coating 15 (FIG. 3). This further protective coating is a porous, heat-resistant metal. In addition to the chromium disclosed in connection with FIG. 3, layer 15 may, also, be nickel, chrome nickel alloys, gold or silver. The advantage of a further metallic layer 15 (FIG. 3) is additionally the getter effect with respect to catalyst poisons. Further, the additional coating provides for better mechanical strength and bonding of the electrically insulating coating 14. It is believed that the equalization of temperature over the entire length of the sensor, due to the good heat conductivity of the metal also has an effect, which desirably improves the overall performance and life of the sensor. The thickness of this additional coating 15 is approximately in the same range as the electrically insulating cover coating 14, that is, between 0.1 and 500 $\mu$ m. These coatings are applied by sintering, flame spraying, plasma spraying, by means of thin film technology, thermal evaporation, vaporization, cathodic decomposition, precipitation from the gas phase, chemical reduction, or by galvanic deposition.

The getter effect with respect to catalyst poisons, which interfere with the catalytic activity of the electron conductive layer 13, can be enhanced by suitably inpregnating layer 15 with substances which act as getters for catalyst poisons. These getter substances may be applied also to the porous electrically insulating cover layer 14. Catalyst poisons which are desirably tied up or removed by the getter impregnants are: heavy metals such as lead, copper, zinc, as well as non-metals such as sulphur and halogen compounds. Getters, or getter substances which can be used as impregnants are: gold, silver, nickel and/or nickel oxide and silicon dioxide. Impregnation by gold or silver can be carried out, in known manner, by quick dipping of the object to be impregnated into a salt solution containing gold, or silver, with subsequent reduction of the salt to the metal by heating. Impregnation with a nickel/nickel oxide system can be carried out by electro-less nickel-coating the substance to be impregnated, and then heating to about 800° C. Impregnation by means of silicon dioxide can be carried out by treating the object to be impregnated with a colloidal solution of silicon dioxide and subsequent firing of the very fine silicon dioxide powder. The method of making the layers 13' and 14' of FIG. 2 will be described in the following: Those parts of the outer surface of the solid electrolyte tube 10 which shall not be covered with platinum are concealed with a mask. A platinum suspension in oil is then sprayed onto those parts of the surface which are not concealed by the mask, so that a platinum layer with a 10 μ m thickness will be formed. After spraying the mask is removed from the solid electrolyte tube 10 and the tube 10 with the platinum layer 13 and the conductor strip 20 is then sintered at a temperature of 1300° C for one hour. During this sintering process the pores are formed, one part of which being micropores, another part being macropores with a diameter greater than one half of the thickness of the layer 13. A porous layer 14 of magnesium spinel $MgAl_2O_4$, 100 μ m thick, is then sprayed on the layer 13, the conductor strip 20 and the remaining surface of the tube 10 not covered with platinum by plasma spraying technique using a magnesium spinel-spraying powder with a grain size of 20 to 40 μ m.

We claim:

1. Electro-chemical sensor to determine oxygen concentration in hot internal combustion exhaust gases comprising a closed, tubular element comprising a solid oxygen ion conductive electrolyte which includes a first tubular portion having a closed end and adapted to be exposed to the exhaust gases, and a second connecting tubular portion integral with said first tubular portion for providing an electrical connection to said first tubular portion, said connecting portion having an outwardly extending flange therearound;

an electron-conductive layer on the inner surface of said solid electrolyte of at least a part of said first tubular portion;

and outer electron conductive layer on at least a part of the outer surface of said solid electrolyte of said first tubular portion, said outer conductive layer being of a material which catalyzes the formation from said hot exhaust gases of those compounds that are thermodynamically stable at the exhaust gas temperature, said outer conductive layer having pores or fissures which are of a diameter, or width, not greater than about the thickness of said outer conductive layer;

a porous protective electrically insulating coating covering said outer electron-conductive layer; and an electrically insulating coating covering at least all of the outer surface portions of said solid ion conductive electrolyte of said first tubular portion not covered by said outer conductive layer, and including the outer surface of said tubular element extending up to said flange and covering a portion thereof and all of the outer surface of said solid ion conductive electrolyte of said connecting portion up to and at least adjacent said connecting flange;

whereby the entire outer surface of said solid ion conductive electrolyte which may be exposed to said exhaust gases is covered to prevent direct contact of solid ion conductive electrolyte material with exhaust gases.

2. Sensor according to claim 1, wherein said electron-conductive layer on said outer surface of said solid electrolyte covers only a portion of said solid electrolyte, and wherein said protective coating which extends over those portions of the outer surface of the solid ion conductive electrolyte which are not covered by said outer electron-conductive layer is also porous.

3. Sensor according to claim 2, wherein said porous coating has a thickness of between about 0.1 and 500 μ m and wherein the ratio of thickness of said coating to average diameter of pores is between 2 : 1 and 100 : 1.

4. Sensor according to claim 1, wherein said electron-conductive layer on said outer surface of said solid electrolyte is formed from at least one catalyst material selected from the group consisting of (i) platinum, palladium, and iridium; (ii) alloys formed from at least one of said platinum, palladium, and iridium together with at least one alloying element selected from the group consisting of aluminum, cobalt, chromium, and platinum metals other than platinum, palladium and iridium; (iii) copper-chromium oxide and copper-chromium oxide doped with barium oxide or nickel oxide; and (iv) lanthanum-cobalt oxide and lanthanum-cobalt oxide doped with strontium oxide.

5. Sensor according to claim 4, wherein said electron-conductive layer on said outer surface of said solid electrolyte has an average thickness of between about 0.1 and 50 μ m.

6. Sensor according to claim 4, wherein said electron-conductive outer layer has an average thickness of between about 0.2 and 20 μ m.

7. Sensor according to claim 4, wherein said porous coating has a thickness of between about 0.1 and 500 μ m and wherein the ratio of thickness of said coating to average diameter of pores is between 5:1 and 20:1.

8. Sensor according to claim 7, wherein said porous coating comprises at least one material selected from the group consisting of magnesium spinel, kaolin, and talc.

9. Sensor according to claim 1, wherein said electron-conductive outer layer contains macro-pores or fissures of an average diameter or width from about 0.5 of the thickness of said layer up to about the thickness of said layer, in addition to micropores of an average diameter width up to one half of the thickness of the said layer.

10. Sensor according to claim 1 wherein the said protective insulating coating consists essentially of magnesium spinel.

11. Electro-chemical sensor to determine oxygen concentration in hot internal combustion exhaust gases comprising a closed, tubular element which includes a first tubular portion adapted to be exposed to the exhaust gases and a second portion for making an electrical connection with said first tubular portion comprising a solid oxygen ion conductive electrolyte;

an electron-conductive layer on the inner surface of said solid electrolyte;

an outer electron conductive layer on at least a portion of the outer surface of said solid electrolyte, said outer conductive layer being of a material which catalyzes the formation from said hot exhaust gases of those compounds that are thermodynamically stable at the exhaust gas temperature, said outer conductive layer having pores or fissures which are of a diameter, or width, not greater than about the thickness of said outer conductive layer;

a protective electrically insulating coating covering said outer electron-conductive layer; and an electrically insulating coating covering at least all of the outer surface portions of said solid ion conductive electrolyte of said first tubular portion not covered by said outer conductive layer, at least the portion of said protective electrically insulating coating covering said outer electron-conductive layer being porous, whereby the entire outer surface of said solid ion conductive electrolyte which may be exposed to said exhaust gases is covered to prevent direct contact of solid ion conductive electrolyte material with exhaust gases, said porous protective electrically insulating coating comprising at least one composition selected from the group consisting of magnesium spinel, kaolin, and talc.

12. Sensor according to claim 11, wherein said porous coating also contains at least one flux selected from the group consisting of feldspar, nepheline-syenite, and wollastonite.

13. Sensor according to claim 11, wherein said electrically insulating coating is impregnated with a getter material which is a getter for catalyst poisons selected from the group consisting of lead, copper, zinc, sulphur and halogen compounds, and wherein said getter material is at least one material selected from the group consisting of gold, silver, nickel, nickel-oxide, and silicon dioxide.

14. Electro-chemical sensor to determine oxygen concentration in hot internal combustion exhaust gases comprising a closed, tubular element which includes a first tubular portion adapted to be exposed to the exhaust gases and a second portion for making an electrical connection with said first tubular portion comprising
a solid oxygen ion conductive electrolyte;
an electron-conductive layer on the inner surface of said solid electrolyte;
an outer electron conductive layer on at least a portion of the outer surface of said solid electrolyte, said outer conductive layer being of a material which catalyzes the formation from said hot exhaust gases of those compounds that are thermodynamically stable at the exhaust gas temperature, said outer conductive layer having pores or fissures which are of a diameter, or width, not greater than about the thickness of said outer conductive layer;
a protective electrically insulating coating covering said outer electron-conductive layer;
an electrically insulating coating covering at least all of the outer surface portions of said solid ion conductive electrolyte of said first tubular portion not covered by said outer conductive layer, at least the portion of said protective electrically insulating coating covering said outer electron-conductive layer being porous, whereby the entire outer surface of said solid ion conductive electrolyte which may be exposed to said exhaust gases is covered to prevent direct contact of solid ion conductive electrolyte material with exhaust gases; and
at least said coated first tubular element has an outer protective coating of at least one porous metal selected from the group consisting of nickel, chromium, nickel-chromium alloys, silver, and gold.

15. Sensor according to claim 1, wherein said outer protection coating has a thickness of between 0.1 to 500 $\mu$ m.

16. Sensor according to clain 15, wherein said porous protective covering is impregnated with a getter material which is a getter for catalyst poisons selected from the group consisting of lead, copper, zinc, sulphur and halogen compounds, and wherein said getter material is at least one material selected from the group consisting of gold, silver, nickel, nickel-oxide, and silicon dioxide.

17. Electro-chemical sensor to determine oxygen concentration in hot internal combustion exhaust gases comprising
a closed tubular element comprising a solid oxygen ion conductive electrolyte having a closed end and adapted to be exposed to the exhaust gases, and a second connecting tubular portion integral with said first tubular portion for providing an electrical connection with said first tubular portion, said connecting portion having an outwardly extending flange therearound;
an electron-conducting metal coating on the inner surface of said electrolyte of at least a portion of said first tubular portion;
an electron-conducting outer layer of a material which catalyzes the formation from said hot exhaust gases of compounds that are thermodynamically stable at the exhaust gas temperature, between 0.1 and 50 $\mu$ m thick and having pores of fissures which are of a diameter, or width, up to about the thickness of said layer covering at least a part of the outer surface of said solid electrolyte; and
a porous protective coating between 0.1 and 500 $\mu$ m thick and having a ratio of thickness to average diameter of pores of between 2:1 and 100:1 on said electron-conductive outer layer and also covering at least all of the outer surface portions of said solid ion conductive electrolyte of said first tubular portion not covered by said outer conductive layer and including the outer surface of said tubular element extending up to said flange and covering a portion thereof and covering all of the outer surface of said solid ion conductive electrolyte of said connecting portion up to and at least adjacent said connecting flange whereby the entire outer surface of said solid ion conductive electrolyte which may be exposed to said exhaust gases is covered to prevent direct contact of solid ion conductive electrolyte material with exhaust gases.

18. Sensor according to claim 17, wherein said electron-conducting outer layer covers all of the outer surface of said solid ion conductive electrolyte of said first tubular portion.

19. Sensor according to claim 18 wherein said porous protective covering is impregnated with a getter material, said getter material is at least one material selected from the group consisting of gold, silver, nickel, nickel-oxide, and silicon dioxide.

20. Sensor according to claim 17, wherein said electron-conductive layers are composed of a platinum metal and at least said electron-conducting outer layer contains macro-pores or fissures of an average diameter width from about 0.5 to the thickness of said layer up to about the thickness of said layer, in addition to micropores of an average diameter width up to one half of the thickness of said layer.

21. Sensor according to claim 20 wherein the said protective insulating coating consists essentially of magnesium spinel.

22. Sensor according to claim 17 wherein said porous coating comprises at least one material selected from the group consisting of magnesium spinel, kaolin, and talc.

23. Sensor according to claim 17 wherein said electron-conducting outer layer has a thickness between about 0.2 and 20 $\mu$ m.

24. Sensor according to claim 23 wherein said electron-conducting outer layer is a platinum metal layer.

25. Sensor according to claim 24 wherein the ratio of thickness of said porous protective coating to said electron-conductive outer layer is between 5:1 and 20:1.

26. Sensor according to claim 17 wherein the said protective insulating coating consists essentially of magnesium spinel.

* * * * *